US011833290B2

(12) United States Patent
Locke et al.

(10) Patent No.: US 11,833,290 B2
(45) Date of Patent: Dec. 5, 2023

(54) DRESSING DESIGN INCORPORATING FORMED 3D TEXTILE FOR THE DELIVERY OF THERAPEUTIC NEGATIVE PRESSURE AND COMPRESSIVE FORCES TO A TREATMENT SITE

(71) Applicant: KCI Licensing, Inc., San Antonio, TX (US)

(72) Inventors: Christopher Brian Locke, Bournemouth (GB); Timothy Mark Robinson, Blandford Forum (GB)

(73) Assignee: KCI Licensing, Inc., San Antonio, TX (US)

( * ) Notice: Subject to any disclaimer, the term of this patent is extended or adjusted under 35 U.S.C. 154(b) by 38 days.

(21) Appl. No.: 17/081,261

(22) Filed: Oct. 27, 2020

(65) Prior Publication Data

US 2021/0128804 A1    May 6, 2021

Related U.S. Application Data

(60) Provisional application No. 62/929,197, filed on Nov. 1, 2019.

(51) Int. Cl.
*A61M 1/00* (2006.01)
*A61F 13/00* (2006.01)
*A61F 13/02* (2006.01)

(52) U.S. Cl.
CPC ......... *A61M 1/90* (2021.05); *A61F 13/00068* (2013.01); *A61F 13/0216* (2013.01)

(58) Field of Classification Search
CPC .. A61M 1/90; A61F 13/00068; A61F 13/0216
See application file for complete search history.

(56) References Cited

U.S. PATENT DOCUMENTS 1,355,846 A    10/1920 Rannells
2,547,758 A     4/1951 Keeling
(Continued)

FOREIGN PATENT DOCUMENTS

AU    550575 B2    3/1986
AU    745271 B2    3/2002
(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
(Continued)

*Primary Examiner* — Kai H Weng
*Assistant Examiner* — Nhu Q. Tran

(57) ABSTRACT

A system for applying negative pressure to a joint positioned in a treatment area. The system includes a negative pressure dressing. The negative pressure dressing includes a compressive layer and a sealing layer. The compressive layer includes a first surface and a second, treatment area-facing. The compressive layer further includes a first elongated portion configured to be positioned proximate the joint. The first elongated portion includes a first end and a second end. The compressive layer further includes a second elongated portion spaced from the first elongated portion and configured to be positioned proximate the joint. The second elongated portion includes a first end and a second end. The compressive layer further includes an interconnecting portion extending between the first elongated portion and the second elongated portion. The interconnecting portion is configured to overlie at least a portion of the joint. The compressive layer further includes a plurality of channels formed in the first surface and extending proximate the (Continued)

second surface. The plurality of channels is formed in at least one of the first end and the second end of the first elongated portion and at least one of the first end and the second end of the second elongated portion. The sealing layer is configured to form a seal around a perimeter of the negative pressure dressing.

19 Claims, 7 Drawing Sheets

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2009/0293887 A1* | 12/2009 | Wilkes ............... A61F 13/00017 128/888 |
| 2009/0299341 A1* | 12/2009 | Kazala, Jr. .......... A61F 13/0243 604/543 |
| 2009/0299342 A1* | 12/2009 | Cavanaugh, II ...... A61F 15/008 604/543 |
| 2010/0075168 A1* | 3/2010 | Schaffer ................ C22C 19/055 428/544 |
| 2012/0263928 A1* | 10/2012 | Scholler .................... B32B 5/02 428/212 |
| 2014/0276288 A1* | 9/2014 | Randolph ............ A61H 9/0057 601/152 |
| 2015/0150729 A1* | 6/2015 | Dagger ................... A61M 1/90 604/543 |
| 2017/0007462 A1* | 1/2017 | Hartwell ........... A61F 13/00034 |
| 2019/0117466 A1* | 4/2019 | Kazala, Jr. .......... A61F 13/0216 |
| 2019/0240073 A1* | 8/2019 | Allen ...................... A61F 13/36 |
| 2021/0146022 A1* | 5/2021 | Hunt ....................... A61M 1/90 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |

(56) References Cited

FOREIGN PATENT DOCUMENTS

| | | |
|---|---|---|
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & dated Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C. ® Therapy Clinical Guidelines: A Reference Source for Clinicians; Jul. 2007.

\* cited by examiner

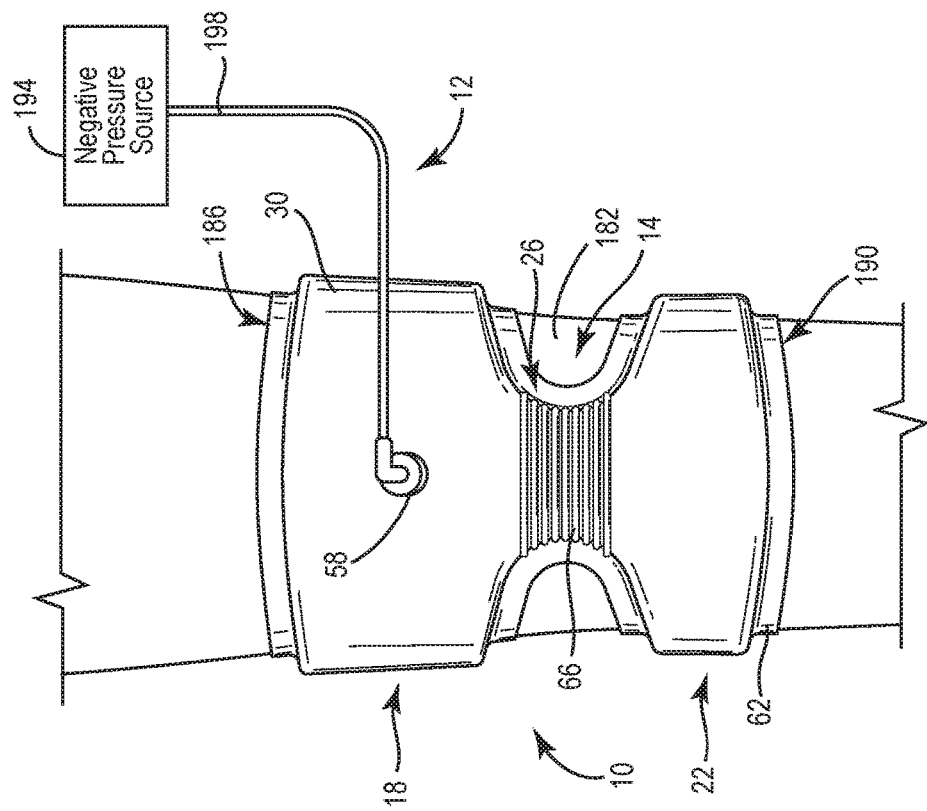
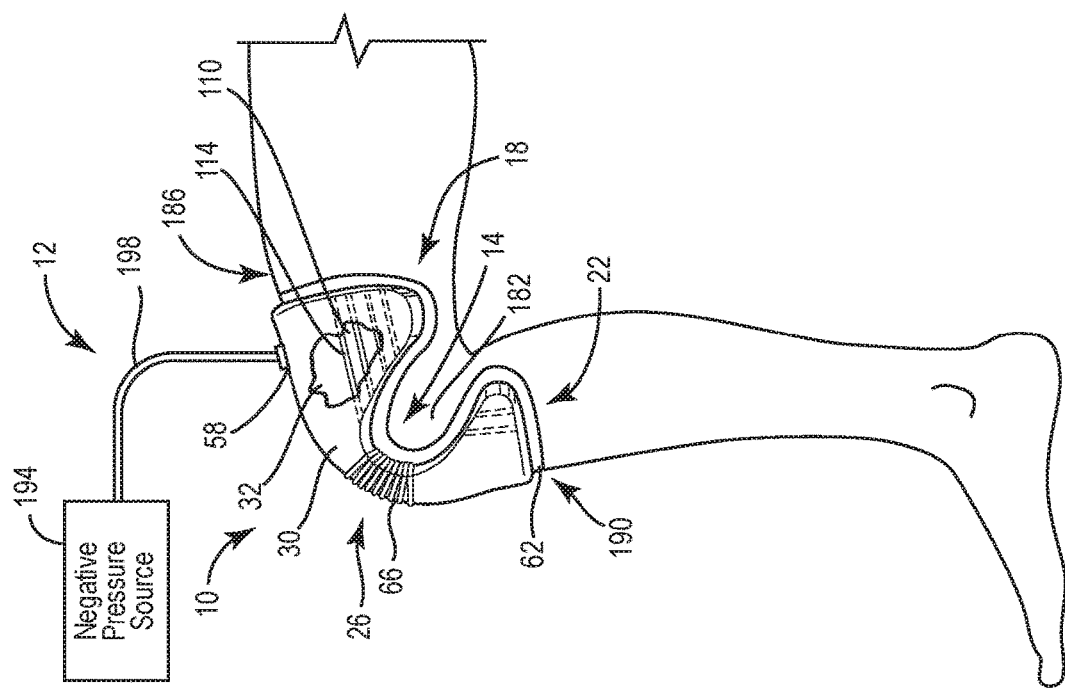
FIG. 8
FIG. 7

DRESSING DESIGN INCORPORATING FORMED 3D TEXTILE FOR THE DELIVERY OF THERAPEUTIC NEGATIVE PRESSURE AND COMPRESSIVE FORCES TO A TREATMENT SITE

CROSS-REFERENCE TO RELATED APPLICATIONS

This application claims the benefit of priority to U.S. Provisional Application No. 62/929,197, filed on Nov. 1, 2019, the complete disclosure of which is hereby incorporated herein by reference in its entirety.

BACKGROUND

The present disclosure relates generally to a negative pressure therapy (NPT) system, and more particularly, to a NPT system adapted to provide NPT to treat joint injuries.

Negative pressure wound therapy (NPWT) is a type of wound treatment therapy that involves applying a negative pressure to a wound site to promote wound. NPWT applies negative pressure to the wound area to drain fluids from the wound area as the wound heals. NPWT can be used to treat a variety of surgical wounds.

SUMMARY

One implementation of the present disclosure is system for applying negative pressure to a joint positioned in a treatment area. The system includes a negative pressure dressing including a compressive layer and a sealing layer. The compressive layer includes a first surface and a second, treatment area-facing surface. The compressive layer further includes a first elongated portion configured to be positioned proximate the joint. The first elongated portion includes a first end and a second end. The compressive layer further includes a second elongated portion spaced from the first elongated portion and configured to be positioned proximate the joint. The second elongated portion including a first end and a second end. The compressive layer further includes an interconnecting portion extending between the first elongated portion and the second elongated portion. The interconnecting portion is configured to overlie at least a portion of the joint. The compressive layer further includes a plurality of channels formed in the first surface and extending proximate the second surface. The plurality of channels is formed in at least one of the first end and the second end of the first elongated portion and at least one of the first end and the second end of the second elongated portion. The sealing layer is configured to form a seal around a perimeter of the negative pressure dressing.

Another implementation of the present disclosure is a system for applying a negative pressure to a joint positioned in a treatment area. The system includes a negative pressure dressing including a compressive layer and a sealing layer. The compressive layer includes a first surface and a second, treatment area-facing surface. The compressive layer further includes a first layer having first material properties. At least a portion of the first layer forms the second surface of the compressive layer. The compressive layer further includes a plurality of ribs formed on the first layer. The plurality of ribs has second material properties. The plurality of ribs is spaced apart by a plurality of channels. The plurality of ribs form the first surface of the compressive layer. The sealing layer overlies the first layer and the second layer. The compressive layer is configured to collapse in a substantially vertical direction and then collapse in a substantially horizontal direction upon application of the negative pressure.

Another implementation of the present disclosure is a system for applying negative pressure to a joint positioned in a treatment area. The system includes a negative pressure dressing and a negative pressure source. The negative pressure dressing includes a compressive layer and a sealing layer. The compressive layer includes a first surface and a second, treatment area-facing surface. The compressive layer is configured for compression in at least a substantially vertical direction and a substantially horizontally direction. The compression in the substantially horizontal direction is larger than the compression in the substantially vertical direction. The compressive layer further includes a first portion including the second surface and a second portion vertically spaced from the first portion and substantially parallel to the first portion. The sealing layer is configured to form a seal around a perimeter of the negative pressure dressing. The negative pressure source is in fluid communication with the negative pressure dressing and configured to apply a negative pressure to the compressive layer to compress at least the compressive layer.

Another implementation of the present disclosure is a compressive layer for a negative pressure treatment dressing. The compressive layer includes a first surface and a second, treatment area-facing surface. The compressive layer further includes a first portion and a second portion. The first portion includes the second surface of the compressive layer. The first portion has a first compression modulus in a substantially horizontal direction and a second compression modulus in a substantially vertical direction. The first compression modulus is smaller than the second compression modulus. The second portion extends from the first portion and includes the first surface of the compressive layer. The second portion has a first compression modulus in a substantially horizontal direction. The first compression modulus of the second portion is different than the first compression modulus of the first portion.

Another implementation of the present disclosure is a system for applying negative pressure to a joint positioned in a treatment area. The system includes a negative pressure dressing and a negative pressure source. The negative pressure dressing includes a compressive layer and a sealing layer. The compressive layer includes a first surface and a second, treatment area-facing surface. The compressive layer further includes a first portion including the second surface of the compressive layer. The first portion has a first compression modulus in a direction substantially parallel to the treatment area and a first thickness substantially perpendicular to the treatment area. The compressive layer further includes a second portion including the first surface of the compressive layer. The second portion has a first compression modulus in the direction substantially parallel to the treatment area and a second thickness in the direction substantially perpendicular to the treatment area. The second thickness is smaller than the first thickness and the second compression modulus is different than the first compression modulus. The sealing layer is configured to overlie the compressive layer and to form a seal around a perimeter of the compressive layer. The negative pressure source is in fluid communication with the negative pressure dressing and configured to apply a negative pressure to the compressive layer to compress at least the compressive layer.

Those skilled in the art will appreciate that the summary is illustrative only and is not intended to be in any way limiting. Other aspects, inventive features, and advantages of the devices and/or processes described herein, as defined solely by the claims, will become apparent in the detailed description set forth herein and taken in conjunction with the accompanying drawings.

BRIEF DESCRIPTION OF THE FIGURES

FIG. 7 is a side view of the negative pressure dressing of FIG. 1 secured to a patient according to an exemplary embodiment.

FIG. 8 is a front view of the negative pressure dressing of FIG. 1 secured to a patient according to an exemplary embodiment.

DETAILED DESCRIPTION

Overview

Referring generally to the FIGURES, a negative pressure dressing for use with a negative pressure system for treating injuries to joints is shown, according to various embodiments. More specifically, the negative pressure dressing is primarily intended for treating injuries to joints, such as sprains, or joint conditions such as arthritis, but may be used to treat other injuries under appropriate circumstances. The negative pressure dressing is described herein in the context of treating a knee joint, but the negative pressure dressing can be used to treat other joints, such as ankle joints, hip joints, wrist joints, elbow joints, and shoulder joints.

The phrase "negative pressure" means a pressure less than an ambient or atmospheric pressure. While the amount and nature of reduced pressure applied to the treatment site can vary according to the application, the reduced pressure typically is between −5 mm Hg and −500 mm Hg and more typically between −100 mm Hg and −300 mm Hg. The negative pressure dressing described herein is shaped to overlie the treatment area, more specifically, proximal portion of the body surface adjacent the joint, the joint, and a distal portion of the body surface adjacent the joint. The negative pressure dressing includes a first elongated portion configured to engage the proximal portion of the body surface, a connecting portion configured to engage the joint, and a second elongated portion configured to engage the distal portion of the body surface.

The negative pressure dressing includes a compressive layer. The compressive layer is formed of a material that collapses laterally and vertically under negative pressure. The compressive layer includes a first elongated portion, connecting portion, and a second elongated portion. A plurality of channels that form a plurality of ribs is formed on ends of the first elongated portion and ends of the second elongated portion to facilitate generally lateral compression under negative pressure. The phrase "channel" means an elongated open top recess that extends longitudinally between the ribs.

When the negative pressure dressing is under negative pressure, the compressive layer first collapses in a generally vertical direction. The compressive layer then collapses in a generally lateral generation, causing bending and puckering of the compressive layer. This bending generates upward lifting forces about substantially a perimeter of the treatment area. The upward lifting forces improve circulation of blood and lymph fluids in the treatment area, reducing swelling and/or inflammation of the treatment site.

Additional features and advantages of the negative pressure therapy system are described in detail below.

Negative Pressure Therapy System

Figure 1:
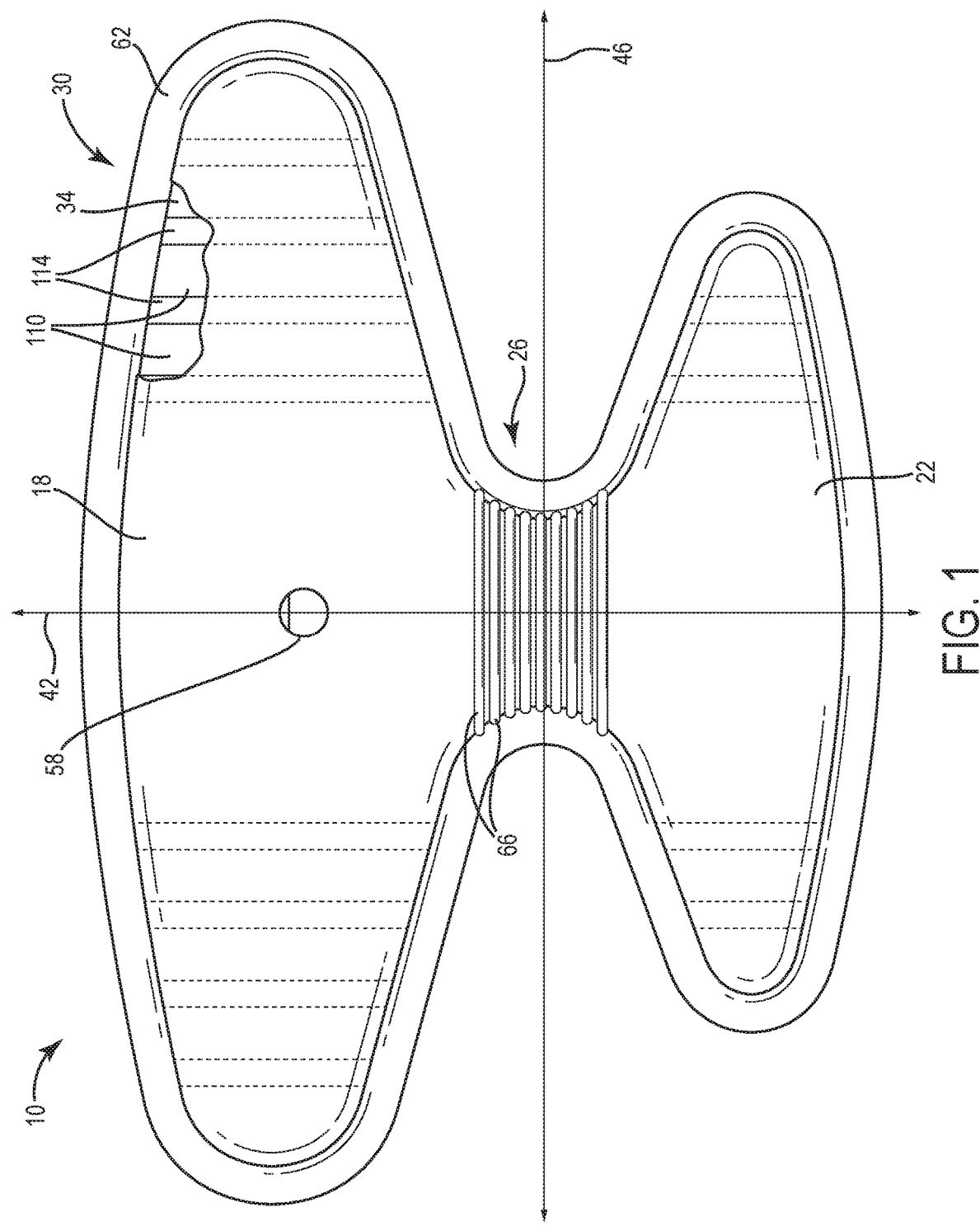
FIG. 1 is a front view of a negative pressure dressing according to an exemplary embodiment.
Figure 2:
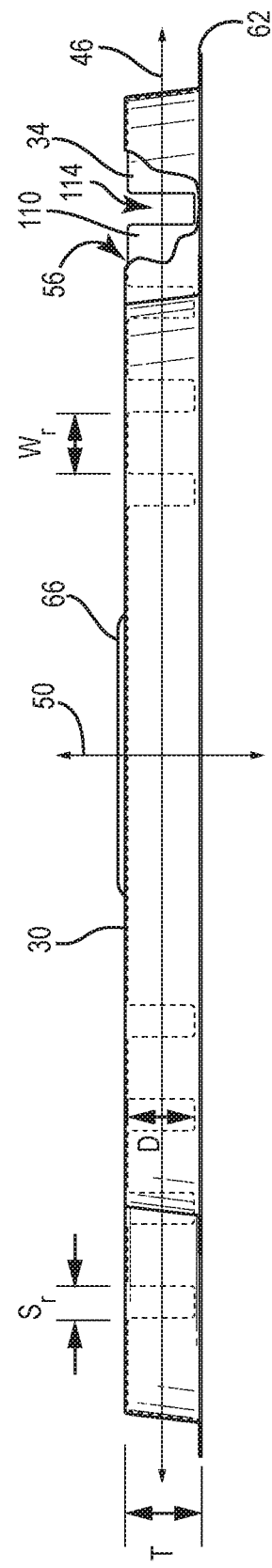
FIG. 2 is a side view of the negative pressure dressing of FIG. 1 according to an exemplary embodiment.
Figure 3:
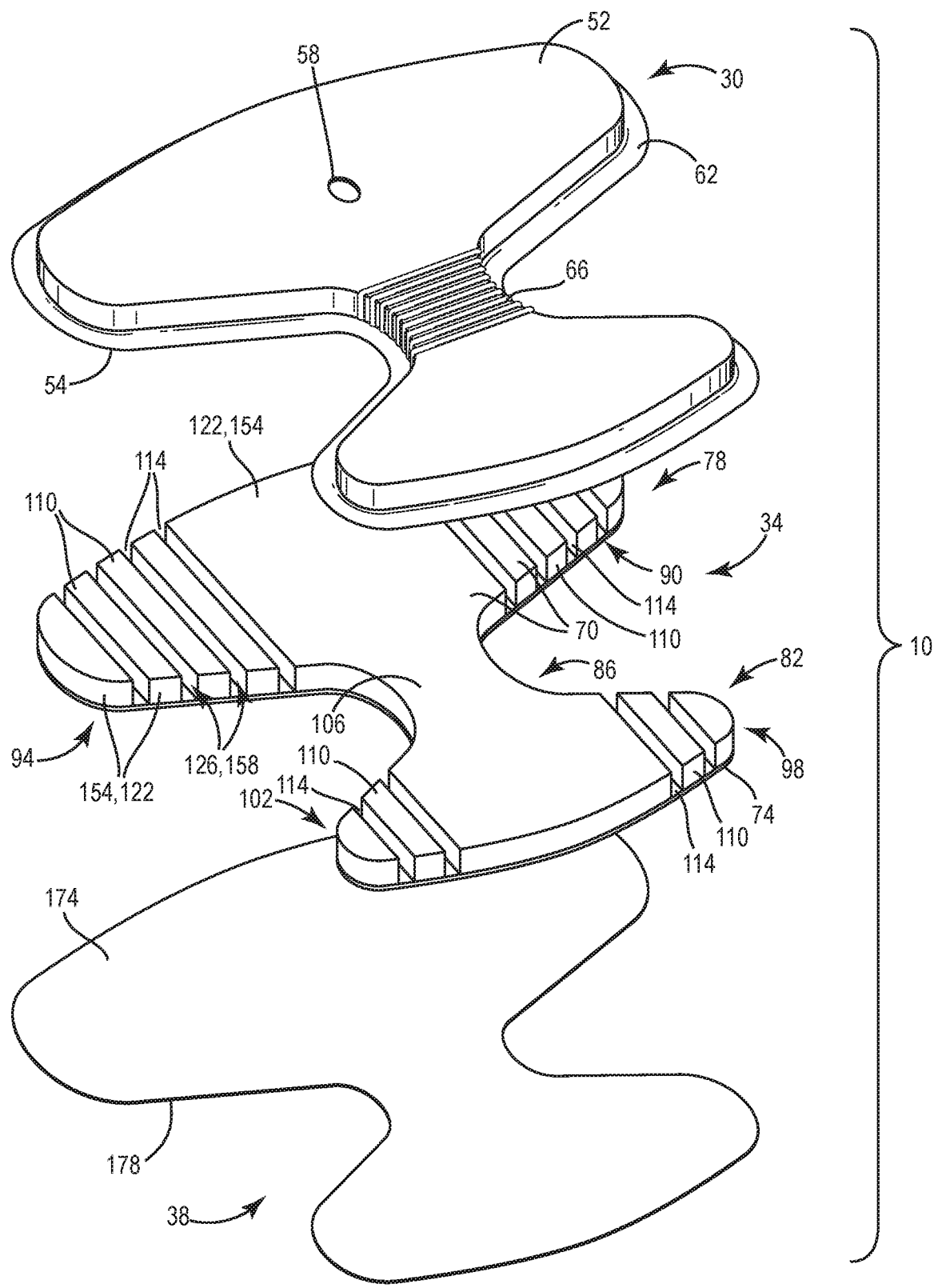
FIG. 3 is an exploded view of the negative pressure dressing of FIG. 1 according to an exemplary embodiment.

Referring to FIGS. 1-3, a negative pressure dressing 10 for use with a negative pressure therapy (NPT) system 12 (FIGS. 7-8) is shown, according to an exemplary embodiment. FIG. 1 is a front view of the negative pressure dressing 10. FIG. 2 is a side view of the negative pressure dressing 10. FIG. 3 is an exploded view of the negative pressure dressing 10. In various embodiments, the negative pressure dressing 10 can be used to treat joint injuries and/or other painful joint conditions. In various embodiments, the negative pressure dressing 10 is applied to intact skin and can be used to treat joints such as knees, ankles, shoulders, elbows, wrists, and hips. The negative pressure dressing 10 is configured to apply a combination of vertical and lateral compression to generate lifting forces within a perimeter of the treatment site. The lifting forces improve circulation of blood and lymph fluid, thereby reducing swelling and/or inflammation proximate the treatment site 14.

In various embodiments, the negative pressure dressing 10 can be formed as a substantially flat sheet. The negative pressure dressing 10 is adapted to conform to treatment sites 14 having high curvature and mobility, such as knee and elbow joints. The treatment site 14 includes the joint, a surface of the body distal to and adjacent the joint, and a surface of the body proximal to and adjacent the joint. The word "distal" is generally used herein to refer to a portion of the body that is away from a center of the body or an attachment point between the body and the limb including. The word "proximal" is generally used herein to refer to a portion of the body that is near a center of the body or is near an attachment point between the body and the limb including the joint.

The negative pressure dressing 10 is adapted to move with the patient as the patient moves the treated joint. The negative pressure dressing 10 includes a first elongated portion 18, a second elongated portion 22, and a connecting portion 26. The first elongated portion 18 and the second elongated portion 22 are generally parallel. The first elongated portion 18 and the second elongated portion 22 are configured to overlie body surfaces adjacent the joint. In the illustrated embodiment, the first elongated portion 18 is longer than the second elongated portion 22. Accordingly, the first elongated portion 18 can overlie a proximal body surface adjacent the joint and the second elongated portion can overlie a distal body surface adjacent the joint since the distal body surface is generally larger than the proximal surface. The connecting portion 26 is configured to overlie the joint. Although the negative pressure dressing 10 is described herein in the context of a knee joint, the negative pressure dressing 10 can also be used to treat ankle joints, hip joints, elbow joints, wrist joints, and shoulder joints.

The negative pressure dressing 10 is shown to include a plurality of layers, including a sealing layer 30, a compressive layer 34, and an optional non-adherent layer 38. The negative pressure dressing 10 includes a longitudinal axis 42 defining a longitudinal direction, a lateral axis 46 defining a lateral direction, and a vertical axis 50 defining a vertical direction. The negative pressure dressing 10 is symmetric about the longitudinal axis 42.

Sealing Layer

With continued reference to FIGS. 1-3, the sealing layer 30 is shown to include a first surface 52 and a second, treatment area-facing surface 54 opposite the first surface 52. When the negative pressure dressing 10 is applied to a treatment area, the first surface 52 faces away from the treatment area, whereas the second surface 54 faces toward the treatment area. The sealing layer 30 supports the compressive layer 34 and the non-adherent layer 38 and provides a barrier to passage of microorganisms through the negative pressure dressing 10. In some embodiments, the sealing layer 30 is an elastomeric material or may be any material that provides a fluid seal. "Fluid seal" means a seal adequate to hold pressure at a desired site given the particular reduced-pressure subsystem involved. The term "elastomeric" means having the properties of an elastomer and generally refers to a polymeric material that has rubber-like properties. Examples of elastomers may include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane, EVA film, co-polyester, and silicones. As non-limiting examples, the sealing layer 30 may be formed from materials that include a silicone, 3M Tegaderm® drape material, acrylic drape material such as one available from Avery, or an incise drape material.

In the illustrated embodiment, the sealing layer 30 defines a cavity 56 (FIG. 3) for receiving the compressive layer 34 and the non-adherent layer 38. As shown in FIG. 3, the compressive layer 34 and the non-adherent layer 38 can have a similar perimeter or profile. As is shown in FIGS. 1 and 3, the first surface 52 of the sealing layer 30 includes a negative pressure port 58 for fluid communication with the NPT system 12 as shown in FIGS. 7-8. In some embodiments, a perimeter of the sealing layer 30 extends beyond (e.g. circumscribes) the perimeter of the compressive layer 34 to provide a margin 62. The second surface 54 of the margin is coated with an adhesive, such as an acrylic adhesive, a silicone adhesive, and/or other adhesives. The adhesive applied to the second surface 54 of the margin 62 is intended to ensure that the negative pressure dressing 10 adheres to the surface of the patient's skin (as shown in FIGS. 7-8) and that the negative pressure dressing 10 remains in place throughout the wear time. The margin 62 may extend around all sides of the compressive layer 34 such that the negative pressure dressing 10 is a so-called island dressing. In other embodiments, the margin 62 and can be eliminated and the negative pressure dressing 10 can be adhered to the surface using other techniques.

As shown in FIGS. 1-3, the first surface 52 of the sealing layer 30 further includes a plurality of articulations 66 proximate the connecting portion 26. The plurality of articulations 66 are positioned to generally overlie the joint and allow more bending and straightening of the joint when the negative pressure dressing 10 is secured to the patient.

The Compressive Layer

Referring to FIG. 3, the compressive layer 34 is shown to include a first surface 70 and a second, treatment area-facing surface 74 opposite the first surface 70. When the negative pressure dressing 10 is applied to a treatment site 14, the first surface 70 faces away from the treatment site 14, and the second surface 74 faces toward the treatment site 14. In some embodiments, the first surface 70 of the compressive layer 34 contacts the second surface 74 of the sealing layer 30. In some embodiments, the second surface 74 of the compressive layer 34 contacts a patient's skin. In embodiments that include the optional non-adherent layer 38, the second surface 74 of the compressive layer 34 contacts the non-adherent layer 38. The compressive layer 34 is adapted to compress under negative pressure. More specifically, the compressive layer 34 is adapted to first collapse in a generally vertical direction defined by the vertical axis 50. The compressive layer 34 is then adapted to collapse in a generally horizontal (e.g., lateral) direction defined by the lateral axis 46 towards the longitudinal axis 42 of the negative pressure dressing 10 and bend upwards, generating lift. This combination of lateral compression and improves circulation and flow of lymph fluids throughout the treatment area, thereby reducing swelling and/or inflammation in the treatment area.

Figure 4:
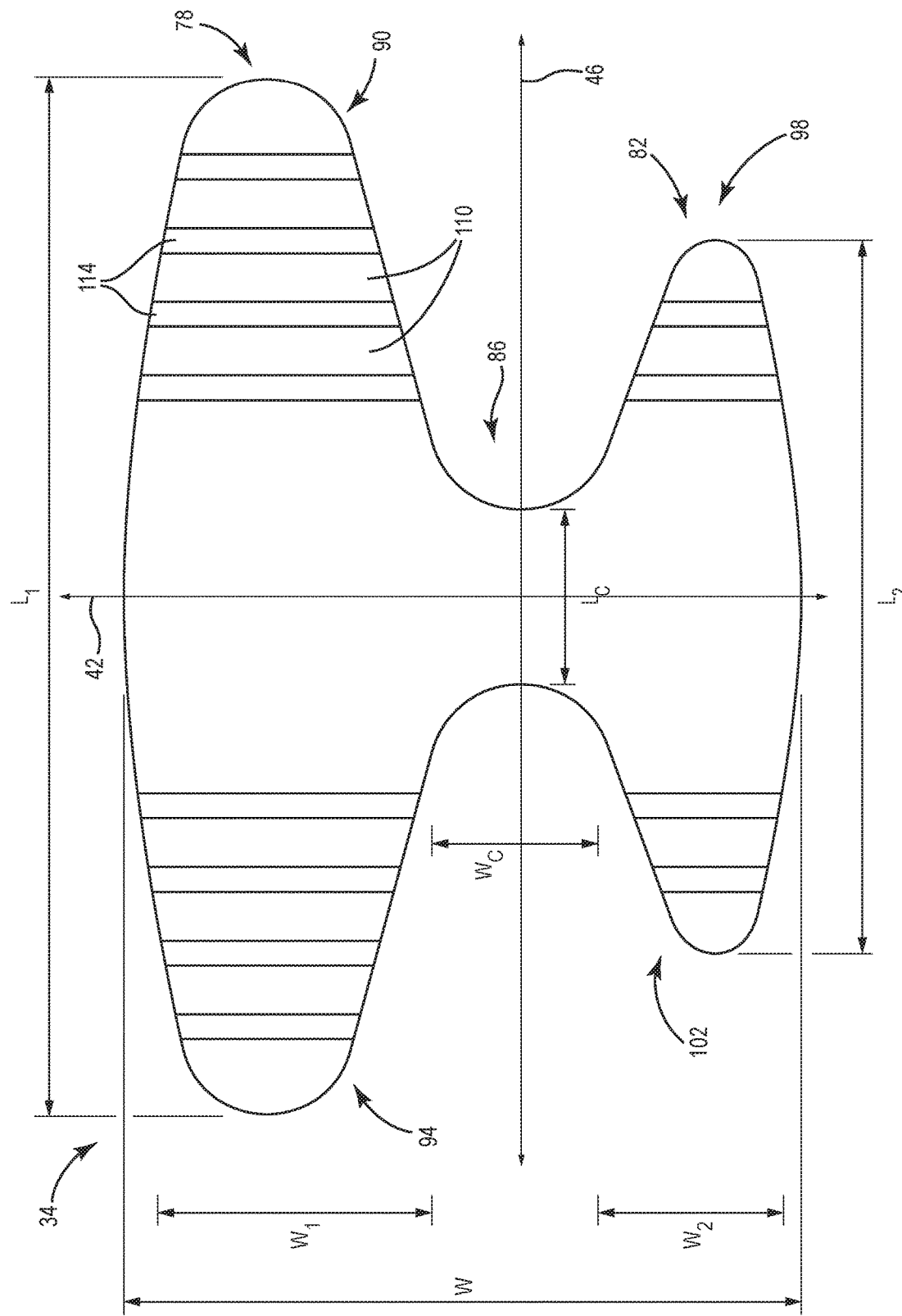
FIG. 4 is a front view of a compressive layer of a negative pressure dressing for use with the negative pressure dressing of FIG. 1 according to some embodiments.

As is best shown in FIG. 4, the compressive layer 34 is generally symmetrical about a longitudinal axis 42 and includes a first elongated portion 78, a second elongated portion 82, and a connecting portion 86 extending between the first elongated portion 78 and the second elongated portion 82. The compressive layer 34 can have a width W that is between approximately 80 mm and approximately 300 mm. The compressive layer 34 can have a thickness T that is between approximately 2 mm and approximately 8 mm. The first elongated portion 78 can have a length $L_1$ that is between approximately 50 mm and approximately 100 mm. The first elongated portion 78 can have a width $W_1$ that is between approximately 40 mm and approximately 80 mm. The second elongated portion can have a length $L_2$ that is between approximately 40 mm and approximately 80 mm. The second elongated portion can have a width $W_2$ that is between approximately 20 mm and approximately 60 mm. The connecting portion 86 can have a length $L_c$ that is between approximately 30 mm and approximately 60 mm. The connecting portion 86 can have a width $W_c$ that is between approximately 30 mm and approximately 50 mm. In the illustrated embodiment, the compressive layer 34 is symmetric about the longitudinal axis 42.

Figure 6:
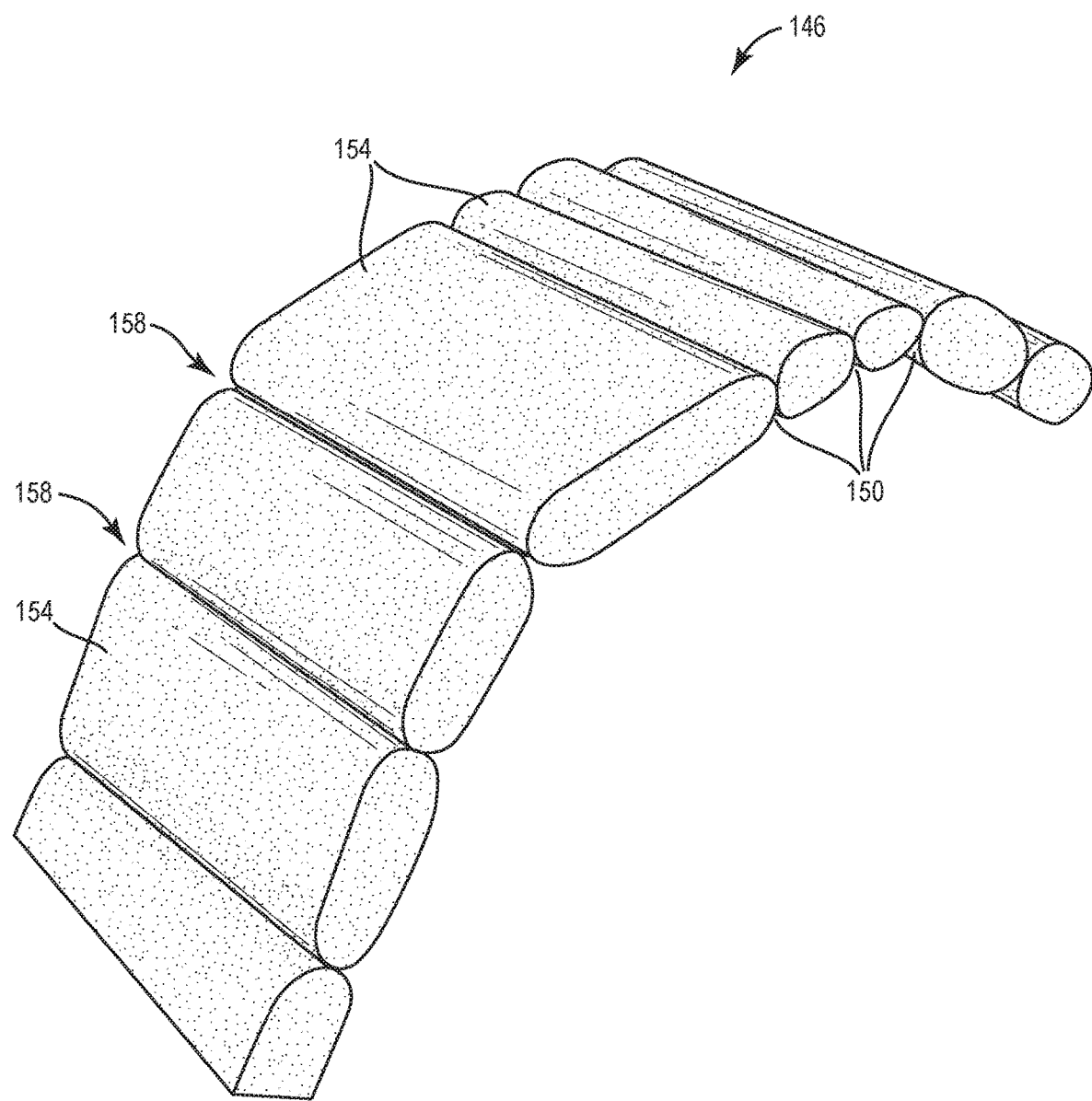
FIG. 6 is a perspective view of a welded foam material for use with the negative pressure dressing of FIG. 1 according to another exemplary embodiment.

The first elongated portion 78 has a first end 90 and a second end 94. The first elongated portion 78 can be wrapped about a first body surface near the joint. More specifically, the first elongated portion 78 is intended to be secured about a proximal body surface proximate the joint. The second elongated portion has a first end 98 and a second end 102. The second elongated portion 22 can be wrapped about a second body surface proximate the joint. As is seen in FIGS. 6-7, the first elongated portion 78 and the second elongated portion 82 are positioned on opposing sides of the joint. A central portion 106 extends between the first end 90 and the second end 94 of the first elongated portion 78, the first end 102 and the second end 102 of the second elongated portion 82, and along the connecting portion 86.

As is best shown in FIGS. 2-4, a plurality of ribs 110 is formed in the first end 90 of the first elongated portion 78, the second end 94 of the first elongated portion 78, the first end 98 of the second elongated portion 82, and the second end 102 of the second elongated portion 82. As shown in FIGS. 2 and 3, a plurality of channels 114 is formed in the first surface 70 of the compressive layer 34 and extend towards the second surface of the compressive layer 34. The plurality of channels 114 form a plurality of ribs 110 between adjacent channels of the plurality of channels 114. The plurality of channels 114 does not extend through the second surface 74. The plurality of channels 114 are elongated open top recesses extending longitudinally between the ribs. The plurality of ribs 110 and the plurality of channels 114 are configured to facilitate lateral compression (e.g., compression towards the longitudinal axis 42 in the lateral direction defined by the lateral axis 46) of the compressive layer 34 by reducing an amount of material present in the first end 90 and second end 94 of the first elongated portion 78 and the first end 98 and the second end 102 of the second elongated portion 82.

In some embodiments, the plurality of channels 114 have a depth D that is between approximately 0.5 cm and approximately 2 cm. In the illustrated embodiment, each of the ribs of the plurality of ribs 110 has a width $W_r$ of approximately 5 mm. In the illustrated embodiment, a spacing (e.g., channel width) $S_r$ between adjacent ribs is approximately 3 mm-4 mm. In other implementations, other dimensions of the depth D, the width $W_r$, and the spacing $S_r$ can be used. For example, in some embodiments, a spacing between the ribs of the plurality of ribs can be graduated to facilitate lateral compression, such that the spacing $S_r$ between adjacent ribs of the plurality of ribs 110 increases in a laterally inward direction. In some embodiments, the width $W_r$ of the ribs the plurality of ribs 110 can be graduated to facilitate lateral compression, such that widths $W_r$ of adjacent ribs of the plurality of ribs 110 decreases in a laterally inward direction. As is described in greater detail below, in some embodiments, the compressive layer 34 can be made of a textile material and the plurality of ribs 110 and the plurality of channels can be knit into the compressive layer 34 by varying the kinit pattern of the textile material. In some embodiments, the compressive layer can be made of a foam material and the ribs can be welded into or cut into the compressive layer 34.

Figure 5:
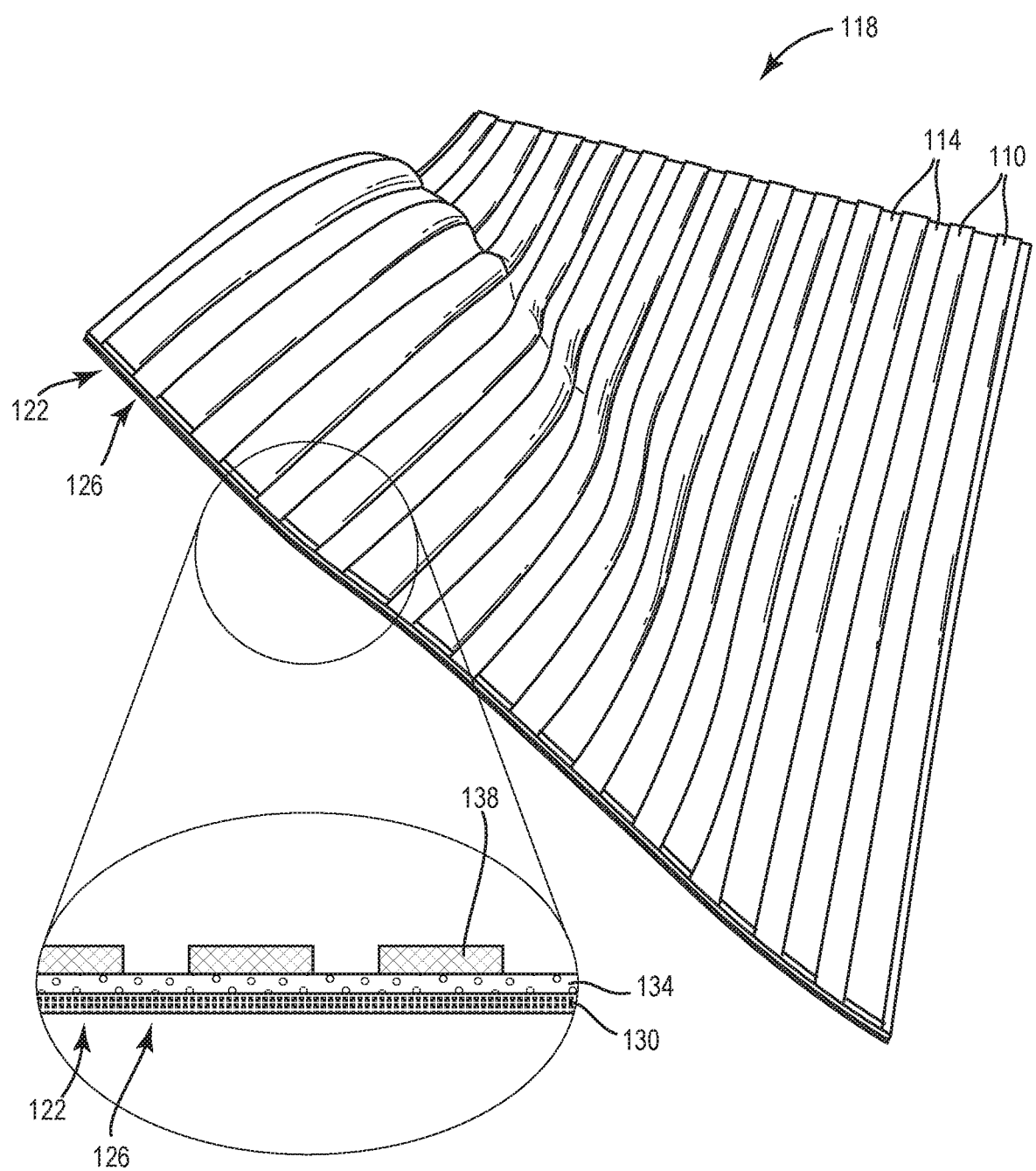
FIG. 5 is a perspective view of a three-dimensional textile for use with the negative pressure dressing of FIG. 1 according to an exemplary embodiment.

As shown in FIG. 5, in some embodiments, the compressive layer 34 can be formed of a three-dimensional (3D) textile material 118 having alternate thick 122 and thin regions 126. One such textile material is Balltex 3520 that is available from W. Ball & Sons, Ltd. Any material or combination of materials can be used for the compressive layer 34 provided that the compressive layer 34 is operable to distribute the reduced pressure and provide a distributed compressive force at the treatment site 14. The textile material 118 can include channels for distributing pressure and/or fluids knit into the textile material 118.

The Balltex 3520 material is a 100% polyester material that has a weight of approximately 300 g/m²-approximately 340 g/m². In some embodiments, at least a portion of the material may be coated to make the at least a portion of the material more or less hydrophilic. An exemplary coating technique is Plasma Coating by P2i Ltd.

As is shown in the inset of FIG. 5, the three-dimensional textile material 118 includes a first portion 130, a interconnecting portion 134, and a second portion 138. In the illustrated embodiment, the first portion 130 forms the second surface 74 of the compressive layer 34, the second portion 138 forms the first portion 130 of the compressive layer 34, and the interconnecting portion 134 that extends between the first portion 130 and the interconnecting portion 134 to secure the first portion 130 and the interconnecting portion 134 together. The first portion 130 and the second portion 138 are substantially parallel. The interconnecting portion 134 is substantially perpendicular to the first portion 130 and the second portion 138. The first portion 130 is a continuous layer configured to abut the patient's skin or the optional non-adherent layer 38.

The textile material 118 is configured to have a vertical compression modulus in a generally vertical direction defined by the vertical axis 50 and a lateral compression modulus in a generally lateral direction defined by the lateral axis 46. In the illustrated embodiment, lateral compression modulus is lower than the vertical compression modulus to facilitate lateral compression. The first portion 130, the interconnecting portion 134, and the second portion 138 can be non-interdependent materials, such that the first portion 130, the interconnecting portion 134, and the second portion 138 can be made of different materials. In some embodiments, the first portion 130, the interconnecting portion 134, and the second portion 138 can have different material properties. For example, in some embodiments, the first portion 130, the interconnecting portion 134, and the second portion 138 can have different textile knit patterns, different weights, different densities, different fibers, and/or different stiffnesses. For example, in some embodiments, the first portion 130 can have a first textile knit pattern including a first plurality of pores (e.g., spaces between textile fibers), the interconnecting portion 134 can have a second textile knit pattern including a second plurality of pores, and the second portion 138 can have a third textile knit pattern including a third plurality of pores. The first knit pattern can have smaller voids (e.g., be a tighter knit) than the third knit pattern and/or the second knit pattern. In some embodiments, the second knit pattern and/or the third knit pattern can have larger voids (e.g., be a looser knit) to reduce a pressure drop across the compressive layer 34. In other embodiments, the first portion 130, the interconnecting portion 134, and the second portion 138 can be made of different materials. In some embodiments, the first portion 130, the interconnecting portion 134, and the second portion 138 can be treated with different materials. For example, in some embodiments, the first portion 130 can be treated to prevent the compressive layer 34 from irritating a patient's skin. The materials and the material properties of the first portion 130, the interconnecting portion 134, and the second portion 138 and the dimensions of the plurality of ribs 110 and the plurality of channels 114 can be varied in different embodiments and/or different applications to customize an amount of lateral compression and lift generated by the compressive layer 34 to a particular joint.

With continued reference to FIG. 5, the three dimensional textile material 118 includes thick regions 122 and thin regions 126. The thick regions 122 form the plurality of ribs 110 and the thin regions 126 form the plurality of channels 114 positioned adjacent the plurality of ribs 110. In some embodiments, the thick region 122 can be formed by the first portion 130, the interconnecting portion 134, and the second portion 138. The thin region 126 can be formed by at least the first portion 130 and can include a portion of the interconnecting portion 134 and/or a portion of the second portion 138. In some embodiments, such as the embodiment shown in FIG. 5, the entire three dimensional textile material 118 can include the thick regions 122 and thin regions 126. In other embodiments, such as the embodiment shown in FIGS. 1-4, the textile material 118 can include the thick region 122 on the central portion 106. The thick region 122 can be formed of the first portion 130, the interconnecting portion 134, and the second portion 138. The textile material 118 can further include the plurality of ribs 110 and the plurality of channels 114 (e.g., the thick regions 122 and the thin regions 126, respectively) proximate the ends 90, 94 of the first elongated portion 78 and the ends 98, 102 of the second elongated portion 82. Such a configuration facilitates a combination of lateral compression and upward bending proximate the ends 90, 94 of the first elongated portion 78 and the ends 98, 102 of the second elongated portion 82, which generates a generally circumferential lifting force around the joint. The lifting force around the joint facilitates circulation and/or lymph flow in the treatment site, reducing swelling and/or inflammation of the treatment site.

As shown in FIG. 6, in some embodiments, the compressive layer 34 can be made from a porous and permeable foam-like material 146 and, more particularly, a reticulated, open-cell polyurethane or polyether foam that allows good permeability of while under a reduced pressure. One such foam material that has been used is the VAC® Granufoam® material that is available from Kinetic Concepts, Inc. (KCI) of San Antonio, Tex. Any material or combination of materials might be used for the compressive layer 34 provided that the compressive layer 34 is operable to distribute the reduced pressure and provide a distributed compressive force along the treatment site.

The reticulated pores of the Granufoam® material 146 that are in the range from about 400 to 600 microns, are preferred, but other materials may be used. The compression modulus of Granufoam at 65% compression is approximately 3 kPa (0.43 psi). The density of the absorbent layer material, e.g., Granufoam® material, is typically in the range of about 1.3 lb/ft$^3$-1.6 lb/ft$^3$ (20.8 kg/m$^3$-25.6 kg/m$^3$). A material with a higher density (smaller pore size) than Granufoam® material may be desirable in some situations. For example, the Granufoam® material or similar material with a density greater than 1.6 lb/ft$^3$ (25.6 kg/m$^3$) may be used. As another example, the Granufoam® material or similar material with a density greater than 2.0 lb/ft$^3$ (32 kg/m$^3$) or 5.0 lb/ft$^3$ (80.1 kg/m$^3$) or even more may be used. The more dense the material is, the higher compressive force that may be generated for a given reduced pressure. If a foam with a density less than the tissue at the tissue site is used as the absorbent layer material, a lifting force may be developed. In one illustrative embodiment, a portion, e.g., the edges, of the negative pressure dressing 10 may exert a compressive force while another portion, e.g., the central portion 106, may provide a lifting force.

Among the many possible compressive layer 34 materials, the following may be used: Granufoam® material or a Foamex® technical foam (www.foamex.com). In some instances it may be desirable to add ionic silver to the foam in a microbonding process or to add other substances to the absorbent layer material such as antimicrobial agents. The absorbent layer material may be isotropic or anisotropic depending on the exact orientation of the compressive forces that are desired during the application of reduced pressure. The compressive layer 34 material may also be a bioabsorbable material.

As shown in FIG. 6, the foam material 146 can be a welded foam material 146 including a plurality of welds 150. The plurality of welds 150 form alternately spaced thick regions (e.g., the foam material 146 extending between the plurality of welds 150) 154 and thin regions 158 defined by the plurality of welds 150. The foam material 146 is configured to have a vertical compression modulus in a generally vertical direction defined by the vertical axis 50 and a lateral compression modulus in a generally lateral direction defined by the lateral axis 46. In the illustrated embodiment, lateral compression modulus is lower than the vertical compression modulus to facilitate lateral compression. The thick regions 154 and the thin regions 158 can have different material properties. For example, in some embodiments, the thin regions 158 and the thick regions 154 can have different densities, and/or different stiffnesses. For example, in the illustrated embodiments, the thin regions 158 are denser than the thick regions 154. The thin regions 158 can therefore generate larger compressive forces in the generally lateral direction defined by the lateral axis 46 than the thick regions 154. The positioning of the plurality of welds 150 (e.g., spacing and number of welds) can be varied in different embodiments and/or different applications to customize an amount of lateral compression and lift generated by the compressive layer 34 to a particular joint.

FIG. 6 illustrates an exemplary foam compressive layer material 146 including the thick regions 154 and the thin regions 158. The thick regions 154 form the plurality of ribs 110 and the thin regions 158 are formed the plurality of welds 150. In the embodiment illustrated in FIG. 6, the plurality of welds 150 forms the plurality of channels 114. In some embodiments, such as the embodiment shown in FIG. 6, the entire three dimensional textile material includes thick regions 154 and thin regions 158. The spacing of the welds of the plurality of welds 158 varies such that the central portion 106 of the foam material 146 is unwelded and a portion of the foam material 146 includes the plurality of welds 150. In embodiments of the negative pressure dressing 10, such as the embodiment shown in FIGS. 1-4, the foam material 146 can include an unwelded portion proximate the central portion 106 the negative pressure dressing 10, and include welded portions proximate the ends 90, 94 of the first elongated portion 18 and the ends 98, 102 of the second elongated portion 22. Such a configuration facilitates a combination of lateral compression and upward bending proximate the ends 90, 94 of the first elongated portion 18 and the ends 90, 94 of the second elongated portion 22, which generates a generally circumferential lifting force around the joint. The lifting force around the joint facilitates circulation and/or lymph flow in the treatment site, thereby reducing swelling and/or inflammation in the treatment site.

In some embodiments, the compressive layer 34 can include a first plurality of voids (e.g., through holes) and an optional second plurality of voids extending between the first surface 70 and the second surface 74. The first plurality of voids and the second plurality of voids can be used with compressive layer 34 made of the textile material 118, the foam material 146 or other materials. The first plurality of voids are positioned proximate the ends 90, 94 of the first elongated portion 78 and the ends 98, 102 of the second elongated portion 82 The first plurality of voids are oriented so that the first plurality of voids open in a direction that is generally parallel to the vertical axis 50. Accordingly, in the illustrated embodiment, the compression in the vertical direction is based on the pores and not the first plurality of voids. The first plurality of voids are elongate in the generally longitudinal direction and have thicknesses oriented generally in the lateral direction. Accordingly, in the presence of negative pressure, the first plurality of voids are configured to collapse laterally towards (e.g. perpendicularly with respect to) the longitudinal axis 42 and in the vertical direction defined by the vertical axis 50. The first plurality of voids can be larger than the second plurality of voids to generate more lateral compression proximate the ends 90, 94 of the first elongated portion 78 and the ends 98, 102 of the second elongated portion 82.

The second plurality of voids can be positioned in the central portion 106 of the compressive layer 34. The second plurality of voids are shaped and/or oriented to provide less compression than the first plurality of voids. For example, in some embodiments, the second plurality of voids could be smaller than the first plurality of voids. In other embodiments, the adjacent voids of second plurality of voids could be spaced further apart than adjacent voids of the first plurality of voids.

Non-Adherent Layer

Referring again to FIG. 3, the non-adherent layer 38 is shown to include a first surface 174 and a second, wound-facing surface 178 opposite the first surface 174. When the negative pressure dressing 10 is applied to the treatment site 14, the first surface 174 faces away from the treatment site, whereas the second surface 178 faces toward the treatment site. In some embodiments, the first surface 174 of the non-adherent layer 38 contacts the second surface 178 of the compressive layer 34. In some embodiments, the second surface 178 of the non-adherent layer 38 contacts the surface of the patient.

The non-adherent layer 38 is made of a material that is fluid-permeable and intended to not irritate the patient's skin. In the illustrated embodiment, the non-adherent layer is a polyester pique-knit textile material, such as Milliken Textile material. In other embodiments, other permeable and non-irritating textile materials can be used. The non-adherent layer 38 can also be treated with antimicrobial materials. In the illustrated embodiment, the non-adherent layer 38 includes silver ions as an antimicrobial material. Other anti-microbial materials may be used in other embodiments.

Deployment of the Treatment Area Therapy System

Referring now to FIGS. 7 and 8, the negative pressure dressing 10 is shown engaged with the treatment site 14 of a patient to provide NPT to the treatment site 14. The treatment site 14 includes a joint 182, a first portion 186 of the surface of the patient adjacent and generally proximal to the joint 182, and a second portion 190 of the surface of the patient adjacent and generally distal to the joint 182. In the illustrated embodiment, the joint 182 is a knee joint. In other embodiments, the joint 182 can be another type of joint, such as an ankle joint, a hip joint, a wrist joint, an elbow joint, or a shoulder joint.

The negative pressure dressing 10 is in fluid communication with the NPT system 12. The NPT system 12 includes a negative pressure source 194, such as a pump, and negative pressure conduit 198 in fluid communication with the negative pressure source 194. The negative pressure dressing 10 is positioned over the treatment site 14 such that the connecting portion 26 is positioned over the knee joint 182. The first elongated portion 78 is secured to the first portion 186 of the surface of the patient. The second elongated portion 82 is secured to the second portion 190 of the surface of the patient. The adhesive of the margin 62 forms fluid-tight seal around a perimeter of the margin 62.

The negative pressure conduit 198 is then engaged with the negative pressure port 58 formed in the sealing layer 30. The negative pressure source 194 is actuated to generate negative pressure within the negative pressure dressing 10. In response to the negative pressure provided by the negative pressure source 194, the compressive layer 34 first contracts in the generally vertical direction and then contracts in the generally lateral direction. The plurality of channels 114 adjacent each rib of the plurality of ribs 110 facilitates a combination of generally lateral contraction and upward bending proximate the ends 90, 94 of the first elongated portion 18 and the ends of the second elongated portion 22. This lateral contraction and bending generates a lifting force about a perimeter of the knee joint 182, which facilitates circulation and/or lymph flow proximate the knee joint 182, thereby reducing swelling and/or inflammation proximate the knee joint 182.

FIG. 7 illustrates the negative pressure dressing 10 secured to a bent knee joint 182. FIG. 8 illustrates the negative pressure dressing 10 secured to a straight knee joint 182. As shown in FIG. 7, the plurality of articulations 66 formed in the sealing layer 30 splay apart to facilitate bending of the knee joint 182. As is shown in FIG. 8, the plurality of articulations 66 are not splayed apart, allowing the negative pressure dressing 10 to lie against the straight knee joint 182.

Configuration of Exemplary Embodiments

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements can be reversed or otherwise varied and the nature or number of discrete elements or positions can be altered or varied. Accordingly, all such modifications are intended to be included within the scope of the present disclosure. As used herein, the term "approximately" may be substituted with "within a percentage of" what is specified, where the percentage includes 0, 1, 4, and 10 percent. The order or sequence of any process or method steps can be varied or re-sequenced according to alternative embodiments. Other substitutions, modifications, changes, and omissions can be made in the design, operating conditions and arrangement of the exemplary embodiments without departing from the scope of the present disclosure.

What is claimed is:

1. A system for applying negative pressure to a joint positioned in a treatment area, the system comprising:
   a negative pressure dressing comprising:
      a compressive layer having a thickness between a first surface and a second, treatment area-facing surface, the compressive layer comprising:
         a first elongated portion configured to be positioned proximate the joint, the first elongated portion including a first end and a second end;
         a second elongated portion spaced from the first elongated portion and configured to be positioned proximate the joint, the second elongated portion including a first end and a second end;
         an interconnecting portion extending between the first elongated portion and the second elongated portion, the interconnecting portion configured to overlie at least a portion of the joint; and
         a plurality of channels having a depth less than the thickness of the compressive layer formed in the first surface of the compressive layer and extending proximate the second surface of the compressive layer, the plurality of channels formed in at least one of the first end and the second end of the first elongated portion and at least one of the first end and the second end of the second elongated portion;
a plurality of ribs formed between adjacent channels of the plurality of channels, wherein a spacing between adjacent ribs of the plurality of ribs increases in a laterally inward direction; and
a sealing layer configured to form a seal around a perimeter of the negative pressure dressing.

2. The system of claim 1, wherein compression of the compressive layer generates a lifting force.

3. The system of claim 1, wherein the plurality of channels is a first plurality of channels and wherein the compressive layer further comprises a second plurality of channels formed in the first surface of the compressive layer and extending proximate the second surface of the compressive layer, the second plurality of channels formed in the other of the first end and the second end of the first elongated portion and the other of the first end and the second end of the second elongated portion.

4. The system of claim 3, wherein compression of the compressive layer proximate the first plurality of channels and the second plurality of channels generates a lifting force configured to substantially surround a circumference of the treatment area.

5. The system of claim 1, wherein the compressive layer is configured for compression in at least a substantially vertical direction and at least a substantially horizontal direction, the compression in the substantially horizontal direction being larger than the compression in the substantially vertical direction so that the compressive layer compresses more in the substantially horizontal direction than in the substantially vertical direction.

6. The system of claim 5, wherein the plurality of channels is configured to facilitate compression in the substantially horizontal direction.

7. The system of claim 1, further comprising a negative pressure source in fluid communication with the negative pressure dressing and configured to apply a negative pressure to the compressive layer to collapse the compressive layer in a substantially vertical direction and then collapse in a substantially horizontal direction.

8. The system of claim 1, wherein the compressive layer is a textile material having a knit pattern, and the plurality of channels is formed by the knit pattern.

9. The system of claim 1, wherein the compressive layer is a foam material and the plurality of channels is formed by a plurality of welds in the foam material.

10. The system of claim 1, wherein the plurality of channels is configured to distribute negative pressure and/or fluids through the compressive layer.

11. The system of claim 1, wherein the second surface of the compressive layer has a first compression modulus in a substantially horizontal direction and a second compression modulus in a substantially vertical direction, the second compression modulus being larger than the first compression modulus so that the second surface of the compressive layer compresses more in the substantially horizontal direction than in the substantially vertical direction.

12. The system of claim 1, wherein the first surface of the compressive layer has a first compression modulus in a substantially horizontal direction and a second compression modulus in a substantially vertical direction, the second compression modulus being larger than the first compression modulus so that the second surface of the compressive layer compresses more in the substantially horizontal direction than in the substantially vertical direction.

13. The system of claim 1, wherein a plurality of articulations is formed in the sealing layer proximate the interconnecting portion.

14. The system of claim 1, wherein the compressive layer further comprises a plurality of ribs formed between the plurality of channels, each of the plurality of ribs isolated from each other and the interconnecting portion by the plurality of channels.

15. A system for applying negative pressure to a joint positioned in a treatment area, the system comprising:
a negative pressure dressing comprising:
a compressive layer having a first surface and a second, treatment area-facing surface, the compressive layer comprising:
a first portion including the second surface of the compressive layer, the first portion of the compressive layer comprising a first textile material and having a first compression modulus in a direction substantially parallel to the treatment area;
a second portion including the first surface of the compressive layer and a plurality of channels forming a plurality of ribs therebetween, the second portion of the compressive layer comprising a second textile material and having a second compression modulus in the direction substantially parallel to the treatment area and the second compression modulus different than the first compression modulus; and
an interconnecting portion disposed between the first portion and the second portion, the interconnecting portion comprising a third textile material;
wherein the plurality of ribs and the plurality of channels are configured to facilitate lateral compression of the compressive layer; and
a sealing layer configured to overlie the compressive layer and to form a seal around a perimeter of the compressive layer; and
a negative pressure source in fluid communication with the negative pressure dressing and configured to apply a negative pressure to the compressive layer to compress at least the compressive layer.

16. The system of claim 15, wherein the second portion of the compressive layer is configured to facilitate compression and bending of the compressive layer around the joint to generate a lifting force.

17. The system of claim 15, wherein the second portion of the compressive layer is configured to facilitate collapse of the compressive layer in the direction substantially perpendicular to the joint.

18. The system of claim 17, wherein the second portion of the compressive layer is configured such that contraction of the second portion of the compressive layer generates a lifting force around the at least a portion of the circumference of the joint.

19. The system of claim 15, wherein the plurality of channels is formed proximate at least one end of the compressive layer to generate a lifting force proximate the plurality of channels.

* * * * *